United States Patent [19]

Coulter et al.

[11] 4,325,909
[45] Apr. 20, 1982

[54] FLUID TRANSFER APPARATUS

[75] Inventors: Wallace H. Coulter, Miami Springs; Walter M. Mena, Hialeah Gardens, both of Fla.

[73] Assignee: Coulter Electronics, Inc., Hialeah, Fla.

[21] Appl. No.: 200,143

[22] Filed: Oct. 24, 1980

[51] Int. Cl.³ .................... G01N 1/14; G01N 35/06
[52] U.S. Cl. ............................. 422/63; 73/864.24; 73/864.25; 141/198; 422/100
[58] Field of Search .................... 422/100, 64, 63; 23/230 R; 141/130, 198; 73/423 A, 425.6, 864.24, 864.25

[56] References Cited

U.S. PATENT DOCUMENTS

| | | | |
|---|---|---|---|
| 3,635,094 | 1/1972 | Oberli | 73/864.24 |
| 3,894,439 | 7/1975 | Ginsberg | 73/864.24 |
| 4,234,538 | 11/1980 | Ginsberg et al. | 422/64 |
| 4,276,051 | 6/1981 | Ginsberg et al. | 422/64 |
| 4,276,260 | 6/1981 | Orbal | 422/64 |

Primary Examiner—Ronald Serwin
Attorney, Agent, or Firm—Silverman, Cass & Singer, Ltd.

[57] ABSTRACT

A vertically and horizontally movable arm structure for fluid transfer is provided with a tubular member for linear oscillation of a holder for a fluid probe; the tubular member can additionally form a conduit for lead wire connected to the fluid probe. Sensors for the vertical position of the arm and the conductor leads from the sensors can be separately mounted and routed so that the sensor leads do not kink or interfere with the motion of the arm.

8 Claims, 6 Drawing Figures

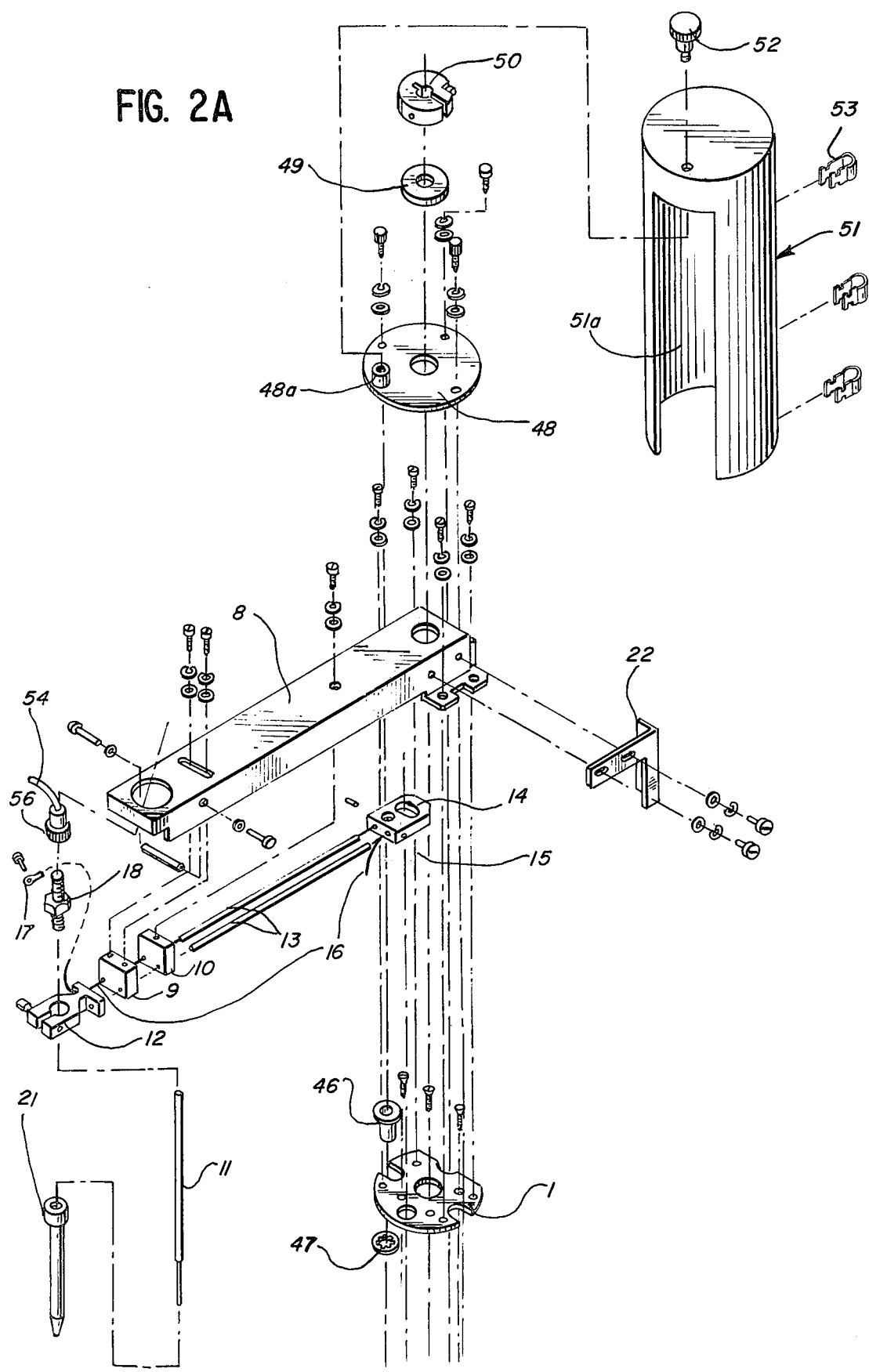

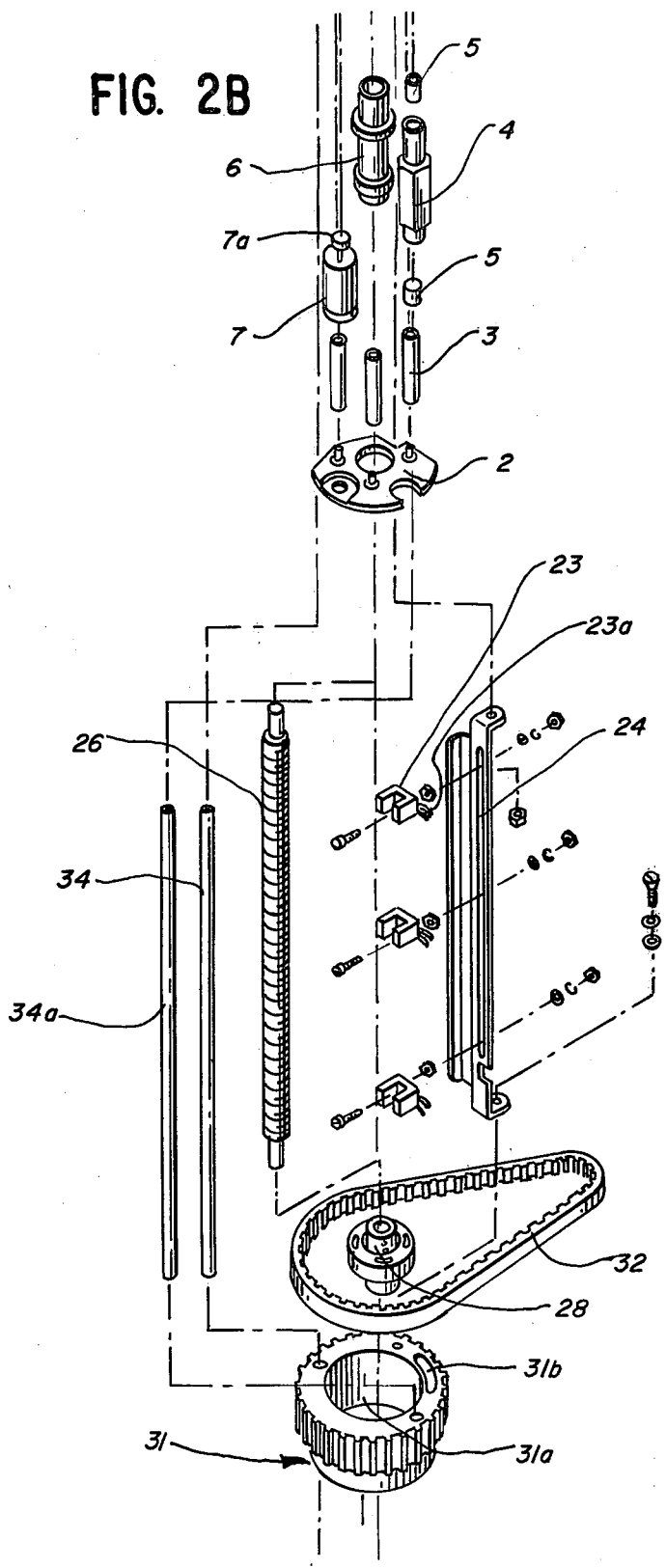

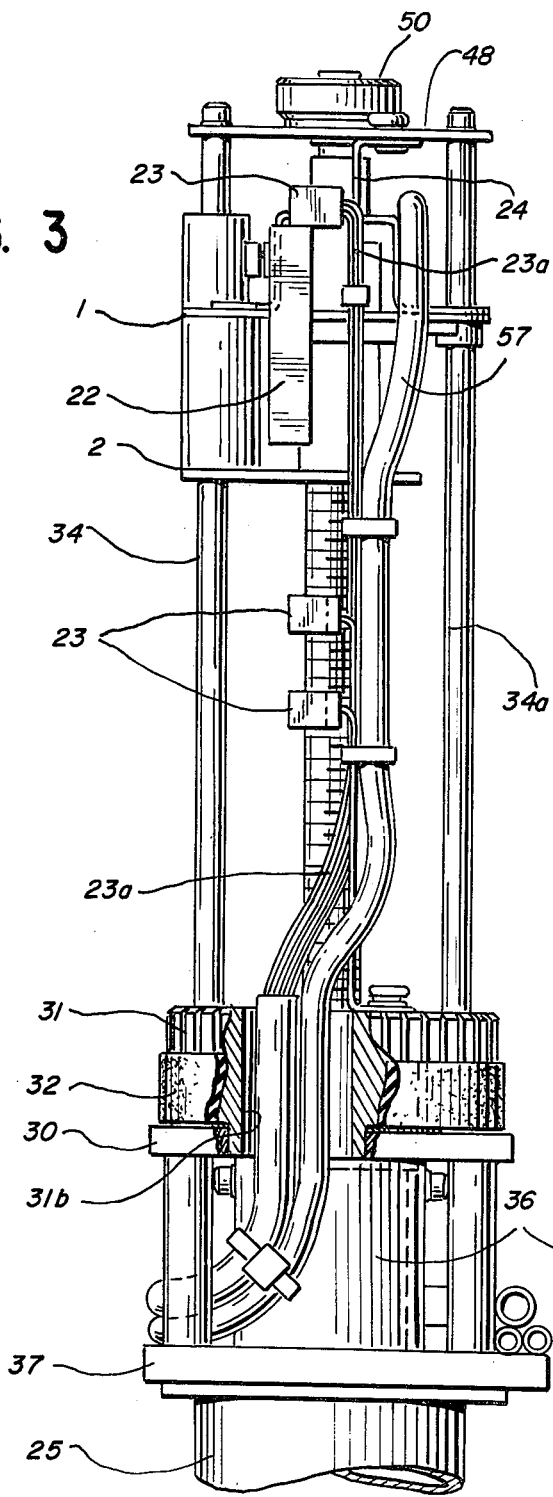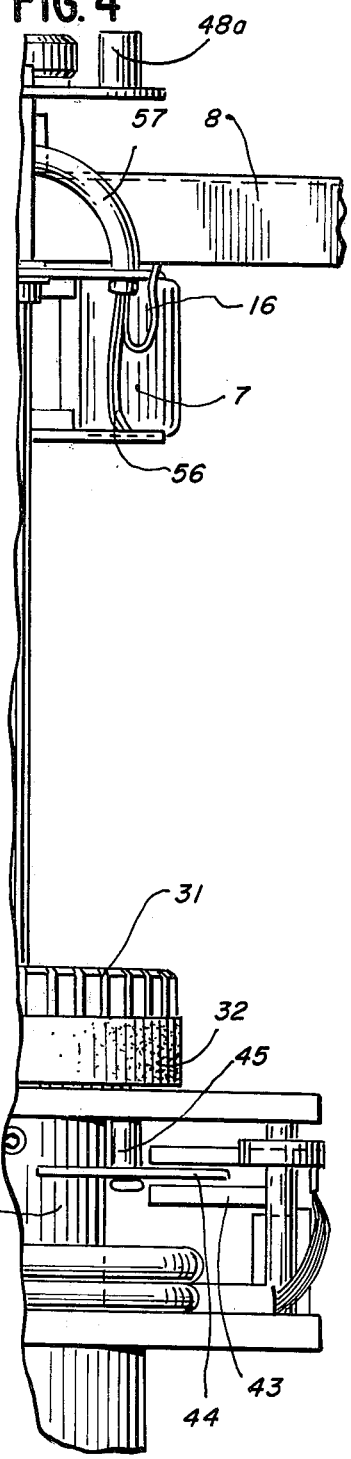

FLUID TRANSFER APPARATUS

BACKGROUND OF THE INVENTION

This invention generally relates to fluid transfer mechanisms for aspirating, transferring, and dispensing fluids, and more particularly to such mechanisms employed in high speed, laboratory analysis instruments.

In modern laboratory analysis, for example analysis of blood serums, large numbers of serum samples, control samples, and reagents must be processed in high speed, automatic equipment. In such equipment, a typical arm mechanism carries a probe for sequentially aspirating multiple fluid aliquots which are then transferred and dispensed into analysis vessels positioned remotely from the aspiration.

In copending United States Patent Application Ser. No. 115,691, filed Jan. 28, 1980, entitled Fluid Transfer Mechanism, now U.S. Pat. No. 4,276,260 which is incorporated herein by reference, DRBAL et al describe a fluid probe carried on an arm mechanism which can be vertically translated at high speed on a high helix shaft and rotated around the shaft by an additional drive. The described probe mechanism further includes a slide structure for stirring fluids by linear oscillation of the probe which also carries connections to a liquid, level-sensing circuit; the arm further includes a light switch which can signal when the light path is interrupted by separately mounted tabs which indicate vertical positions of the arm for monitor and control. Such instruments provide very precise vertical and horizontal positioning of the fluid probe for aspirating and dispensing operations; however, a recurring problem arises in automatic equipment of this type when lead wires of the electrical components are carried on the moving arm, and the motion of the arm or its components causes winding or kinking in lengths of the leads. In extreme situations the motion of the leads can produce resistance or interference with the required motion of the arm.

SUMMARY OF THE INVENTION

In accordance with the fluid transfer mechanism of this invention, a vertically and horizontally movable arm structure is provided with an assembly for oscillation of a fluid transfer probe, in which tubular members linearly oscillate an attached probe mounting member; the tubular member also functions as a conduit for lead wire connected to the probe. The arm structure can include an interrupter member projecting from the end of the arm member opposite the probe for interruption of transmission of a sensor to indicate the vertical position of the arm. The arm structure can cooperate with multiple sensors separately supported in the vertical path of the interrupter member. The pulley member for horizontal rotation of the arm structure can be provided with a through passageway for conduit of electrical wires to eliminate kinking and interference with the motion of the arm.

BRIEF DESCRIPTION OF THE DRAWINGS

FIG. 2A is an exploded, partial perspective view of components of the arm shown in FIG. 1;

FIG. 2B is an exploded, partial perspective view including the vertical sensing structure together with drive and guide shafts of the arm structure shown in FIG. 1;

FIG. 3 is a rear elevation view showing the wiring path of the arm structure shown in FIG. 1;

FIG. 4 is a fragmentary side elevation view of the arm structure shown in FIG. 3.

DESCRIPTION OF THE PREFERRED EMBODIMENTS

Figure 1:
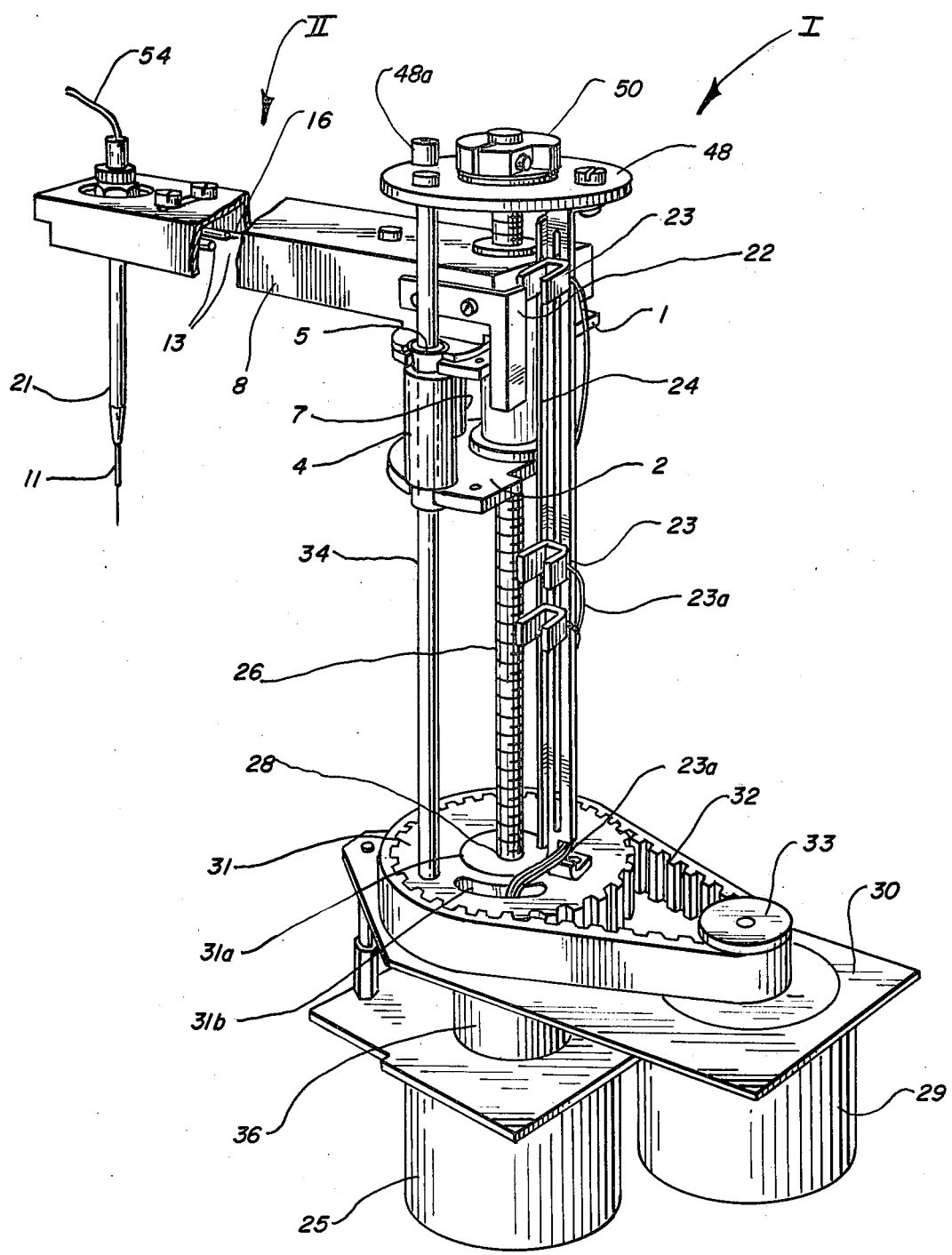
FIG. 1 is a perspective view of the movable arm structure of this invention.

Referring to FIG. 1, a fluid transfer structure in accordance with this invention is generally designated by reference character I and the arm assembly is generally designated by reference character II. The construction of arm assembly II, as most clearly shown in the exploded views of FIGS. 2A and 2B, includes a top support plate 1 and a bottom support plate 2, which together with threaded spacers 3, sandwich three principle components: a bearing support 4 having a bearing 5 pressed into each end for receiving shaft as described hereinafter; a Helix Nut 6; and a stirring motor assembly 7, including an eccentrically located ball bearing 7a.

Mounted to the top surface of the top support plate 1 through four screws is the probe support arm 8. The probe support arm 8 primarily serves to support a linear oscillating assembly, driven by the stirring motor assembly 7 and held from underneath the probe support arm 8 by two small plastic blocks, the front 9 and rear 10 guide supports as best shown in the exploded view of FIG. 2A. The linear oscillating assembly slides back and forth in reaction to the eccentric cam action created by the stirring motor assembly 7.

Referring again to exploded view in FIG. 2A, the linear oscillating assembly includes gear clamp 12 which has two holes to receive the probe guide tubes 13. These tubes are held to gear clamp 12 with adhesive and set screwed 15 to the machined eccentric link 14 at the opposite end. The eccentric link 14 couples the driving force from the stirring motor assembly 7 to the clamped probe 11 by means of tubes 13.

Running through one or both of the hollow probe guide tubes 13 are one or more lead wires 16 which serve as electrical connection from the probe 11 to a suitable electrical, liquid-level sensing circuit (not shown) for detecting the surface of samples or reagents, as more fully described in the aforementioned United States Patent Application Ser. No. 115,691. Wire 16 is connected to a solder-type terminal 17 at the probe end and then further screwed to a threaded stud 18, which in turn is silver soldered to the probe 11 that aspirates and dispenses the fluids. The opposite end of wire 16 is attached to the printed wiring board 19, located behind the arm by a metal bracket 20 shown in FIG. 2C.

The threaded stud 18 is silver soldered to probe 11, and further threaded into a probe housing 21 which serves to protect the probe 11 from damage and also helps maintain its straight extension for entering the narrow width of the cuvette.

When threaded into the probe housing 21 the probe 11 can be securely clamped in the gear clamp 12 of the linear oscillating assembly. The probe 11 and linear oscillating assembly can now be adjusted for position in aspirating and dispensing liquid by mounting screws that attach guide supports 9 and 10 through a slotted hole in the top surface of the probe support arm 8 as shown in both FIGS. 1 and 2A.

As best shown in FIG. 1, a sensor interrupter 22 is bracketed preferably at one side of the rear end of probe support arm 8 so that sensor interrupter 22 travels vertically between the arms of U-shaped light emitting diode (L.E.D.) sensors 23 to interrupt the transmission for indication of a specific vertical position of arm 8 and the tip of probe 11. Sensors 23 are held in position by a slotted vertical sensor bracket 24 which allows vertical adjustment of each sensor 23 independently as shown in FIGS. 1 and 2B.

As arm 8 and attached interrupter 22 move vertically, the sensors 23 and terminals of the electrical leads 23a remain vertically stationary on bracket 24 ensuring that the leads 23a do not kink with the vertical motion of arm 8.

Figure 2C:
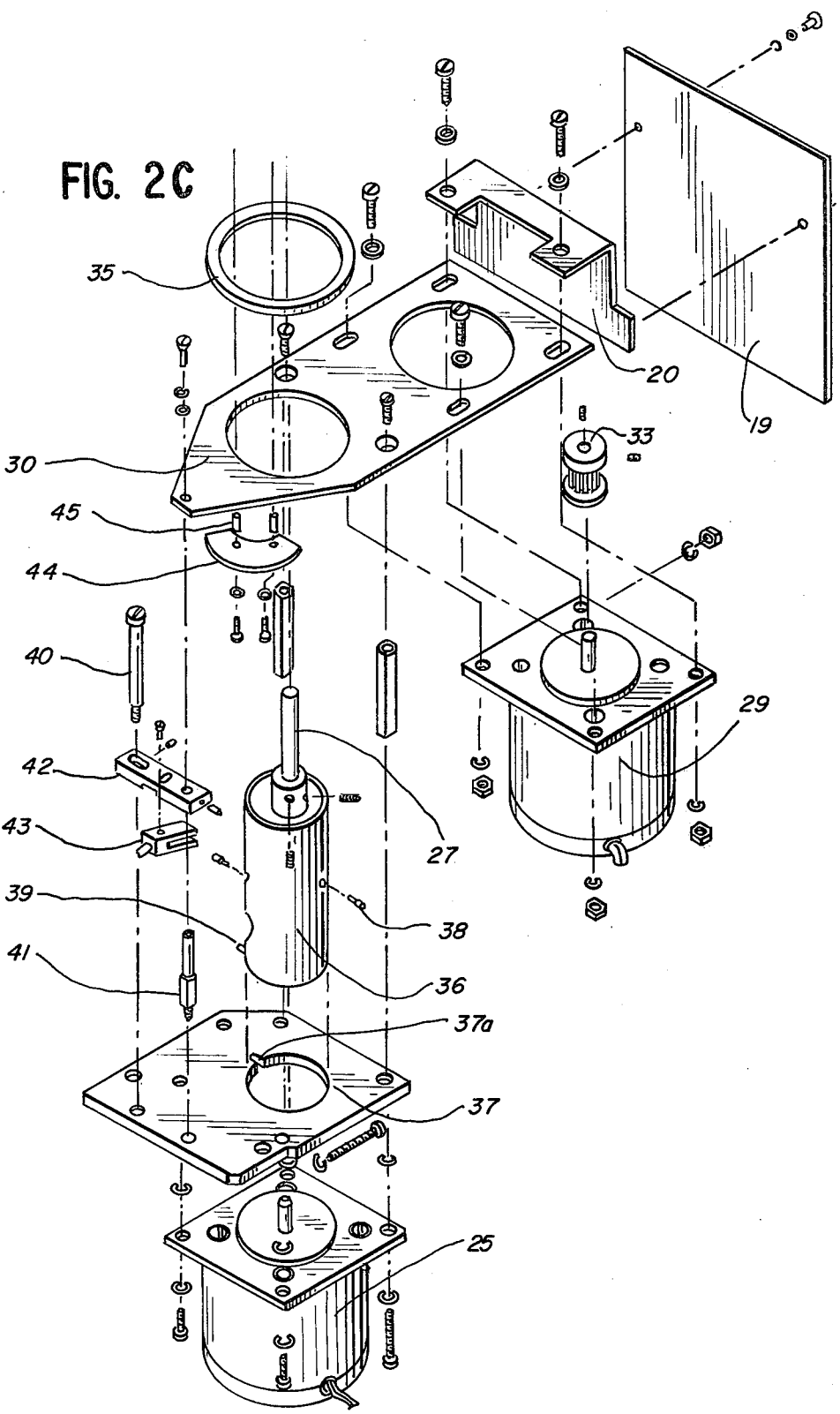
FIG. 2C is an exploded, partial perspective view of the base and drive motors of the arm structure shown in FIG. 1.

The structure of the drive system for the vertical and the horizontal movements of the arm 8 are described with reference to FIGS. 1, 2B and 2C.

Vertical movement is provided by stepper motor 25, which drives the helix shaft 26 through a shaft extension 27 and a coupling 28 which has some lateral flexibility to allow lateral and angular misalignment of the helix shaft 26 as it rotates.

Horizontal movement of arm 8 is provided by a stepper motor 29, mounted to a motor support plate 30, which serves to rotate the pulley 31 through a timing belt 32 and a timing pulley 33, that produces preferably a 4 to 1 gear ratio belt drive system. The lower ends of two guide shafts 34 and 34a are secured in pulley 31 and pass through bearing support 4 and bearing 46, respectively, to rotate plates 1 and 2 and arm 8. Thus, pulley 31 also serves as the main journal type bearing for horizontal movement of arm 8. Pulley 31 is seated on a thin thrust washer 35 that reduces wear and friction between the pulley 31 and the motor support plate 30.

The center hole 31a of pulley 31 receives the outside surface diameter of a lubricated stainless steel sleeve 36, which is secured in a flat plate forming a bearing hub base 37. Plate 37 is keyed to control the assembled location of two tapped holes on opposite sides of the steel sleeve 36 which receive socket head screws 38, serving as mechanical stops for the horizontal movement of pulley 31. The keying is achieved by a small pin 39 pressed into one wall of the sleeve 36 and fitted into a notch 37a in plate 37.

The bearing hub base plate 37 serves to mount the vertical stepper motor 25 and to mount the entire fluid transfer structure I to main frame or similar structure (not shown). Plate 37 is provided with two tapped holes in the front to mount vertical spacers 40, 41 which support a sensor mounting plate 42 holding segmented photoarray sensor 43 as shown in FIG. 2C. As best shown in FIG. 4, photoarray sensor 43 device is of the L.E.D. type and serves to read a coded section 44 that confirms the horizontal position of the tip of probe 11 at fluid pickup, dispense, wash, and oscillation positions. The optically coded section 44 is mounted through small spacers 45 to the threaded bottom surface of pulley 31 and rotates with the movement of pulley 31 in the horizontal mode. Spacers 45 that mount the optically coded section 44 also serve as the contact point for the mechanical stops 38 that limit the movement of the pulley 31 within a suitable angular range.

When assembled, the pulley 31 slips over sleeve 36 and is seated against the thrust washer 35. The helix shaft 26, coupling 28 and shaft extension 27 are joined together and aligned within the center opening of the steel sleeve 36 and set screwed to the vertical motor's shaft 25.

A flanged bearing 46 for shaft 34a is loosely secured with a push-on type of retaining ring 47 to the precision slot located on one side of the top support plate 1 as shown in FIG. 2A.

Referring to FIGS. 1 and 2A, guide shafts 34 and 34a, whose ends are tapped, are capped with a cap plate 48. In addition to transmission of the rotational movement of pulley 31, guide shafts 34 and 34a provide tolerant guidance for the vertical movement of arm 8. A shoulder washer of nylon 49, which acts as a vertical thrust washer and a shaft journal clamp 50 guides vertical float of the top of the helix shaft 26.

As shown in FIG. 2A, a cover 51 with a side opening 51a fits over cap plate 48 and is secured with a thumbscrew 52 to a threaded standoff 48a an cap plate 48. Clips 53 are held through holes in the cover 51 and loosely secure extension (not shown) of tubing 54 to cover 51. The slightly flanged end of tubing 54 provides fluid conduit to probe 11, which protrudes above the top end of the threaded stud 18 and is soldered thereto. Tube 54 is sealed on stud 18 by a knurled cap nut 55.

in the operation of arm 8, the lead wire 16 from probe 11 moves inside the protection of tube 13 during oscillation of probe 11. During vertical movement of arm 8, the motion of wire 16 and lead wires 56 of stirring motor 7 is guided by conduit through a vertically stationary sheath 57 which is preferably attached to sensor bracket 24 as shown in FIGS. 3 and 4. Pulley 31 is provided with a through passageway 31b which provides a conduit for the extensions of wires 16 and 56 within sheath 56 as well as for the extension of sensor leads 23a. The lead extensions passing through passageway 31b remain substantially stationary with respect to the rotation of arm 8 and pulley 31 because passageway 31b is positioned in close radial proximity to the axis of rotation about helix shaft 26 provided by the location of pulley 31.

The embodiments shown in the drawings are illustrative of this invention but do not indicate limitation upon the scope of the claims.

We claim:

1. A vertically and horizontally movable arm structure for fluid transfer, comprising:
   (A) a generally elongate arm member for holding a fluid probe at a distal end thereof; and
   (B) an oscillating assembly mounted to said arm member, for oscillation of said probe to stir fluid into which said probe is inserted, wherein said oscillating assembly includes:
      (1) a mounting member for positioning said probe adjacent said distal end of said arm member;
      (2) at least one tubular member attached to said mounting member and aligned substantially parallel to said arm member; and
      (3) drive means for linear oscillation of said tubular member substantially along the tubular axis thereof, in order to produce oscillation of said attached probe mounting member.

2. The arm structure as claimed in claim 1, further comprising a conductor passing through said tubular member for connection of said probe to a sensing circuit.

3. The arm structure as claimed in claim 1 or 2 wherein said tubular member is positioned below said arm member.

4. The arm structure as claimed in claim 1, further comprising:

an interrupter member projecting from the rear end of said arm member, opposite said distial end, for interruption of electromagnetic transmission positioned such that said interruption indicates the vertical location of said arm member.

5. The arm structure as claimed in claim 4, further comprising:

a support means for positioning one or more sensing means in the vertical path of said interrupter means.

6. The arm structure as claimed in claim 5, wherein said sensing means is adjustably positioned on said support means.

7. The arm structure as claimed in claim 1, further including a pulley member for horizontal rotation of said arm structure wherein said pulley member includes a through passageway for conduit of conductor leads.

8. The structure as claimed in claim 7, wherein said conductor leads include leads connected to sensing means supported separately from said arm member.

* * * * *